(12) United States Patent
Pellacini et al.

(10) Patent No.: US 6,468,979 B1
(45) Date of Patent: Oct. 22, 2002

(54) ERYTHROMYCIN DERIVATIVES WITH ANTIBIOTIC ACTIVITY

(75) Inventors: Franco Pellacini, Milan; Daniela Botta, Como; Enrico Albini, Pavia; Domenico Ungheri, Parabiago, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/744,244

(22) PCT Filed: Jul. 27, 1999

(86) PCT No.: PCT/EP99/05485

§ 371 (c)(1), (2), (4) Date: Jan. 30, 2001

(87) PCT Pub. No.: WO00/06606

PCT Pub. Date: Feb. 10, 2000

(30) Foreign Application Priority Data

Jul. 30, 1998 (IT) .......................................... MI98A1776

(51) Int. Cl.$^7$ .......................... A61K 31/70; C07H 17/08
(52) U.S. Cl. .......................................... 514/29; 536/7.4
(58) Field of Search .............................. 536/7.4; 514/29

(56) References Cited

FOREIGN PATENT DOCUMENTS

WO    WO 96/18633    *   6/1996

OTHER PUBLICATIONS

Gasc et al., "New ether derivatives erythromycin A: a structure–activity relationship study", J. Antibiot., vol. 44(3), 1991, pp. 313–330.

* cited by examiner

*Primary Examiner*—Elli Peselev
(74) *Attorney, Agent, or Firm*—Oblon, Spivak, McClelland, Maier & Neustadt, P.C.

(57) ABSTRACT

Erythromycin derivatives with antibiotic activity and pharmaceutically acceptable salts thereof. A process for preparing such erythromycin derivatives and pharmaceutical compositions containing them as the active principle.

20 Claims, No Drawings

ERYTHROMYCIN DERIVATIVES WITH ANTIBIOTIC ACTIVITY

CROSS-REFERENCE TO RELATED APPLICATIONS

This application is a national-stage filing under 35 U.S.C. 371 of PCT/EP99/05485, filed Jul. 27, 1999, and claims foreign priority benefit to Italy MI 98 001776, filed Jul. 30, 1998.

BACKGROUND OF THE INVENTION

1. Field of the Invention

The present invention relates to compounds with antibiotic activity, which are useful for treating infectious diseases, and relates more particularly to compounds of formula

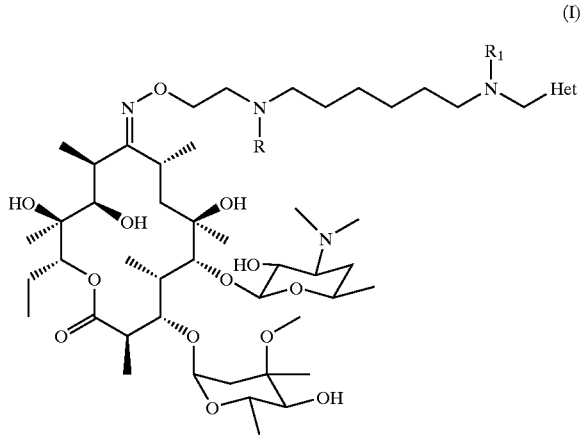

(I)

in which Het is a biheterocyclic system; to pharmaceutically acceptable salts thereof and to pharmaceutical compositions containing them as active principle.

2. Description of Related Art

International patent application WO96/18633 in the name of the Applicant discloses compounds with antibiotic activity, which have the following general formula:

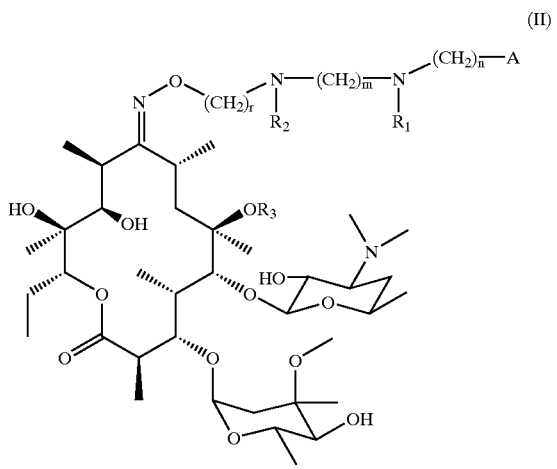

(II)

in which

A is a phenyl or a 5- or 6-membered heterocycle containing one or more hetero atoms chosen from nitrogen, oxygen and sulphur, optionally substituted with 1 to 3 groups, which are the same or different and are chosen from linear or branched $C_1$–$C_4$ alkyl or alkoxy groups, $C_1$–$C_2$ cycloalkenedioxy groups, $C_1$–$C_4$ alkylsulphonyl groups, phenyl, phenoxy, hydroxyl, carboxyl, nitro, halo and trifluoromethyl groups; $R_1$ and $R_2$ are the same or different hydrogen atom or linear or branched $C_1$–$C_4$alkyl group; n is 1 or 2; m is an integer from 1 to 8; r is an integer from 2 to 6; $R_3$ is hydrogen or methyl.

BRIEF SUMMARY OF THE INVENTION

We have now found that, by introducing a biheterocyclic group as a substituent (–A) at the end of the chain in the compounds of formula (II) of the above-mentioned international patent application, it is possible to obtain a class of erythromycin derivatives which have a particularly broad spectrum of activity and a long duration of action, thereby making them extremely useful in antibiotic therapy.

It is an object of the present invention to provide a compound of formula

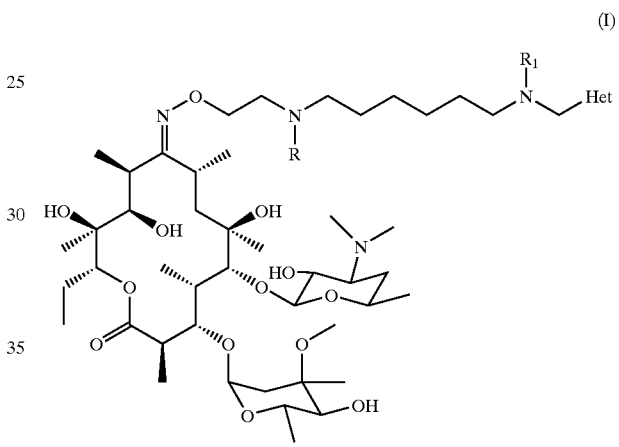

(I)

in which

R and $R_1$ are the same or different hydrogen atom or linear or branched $C_1$–$C_4$ alkyl group; Het is a biheterocyclic group of formula

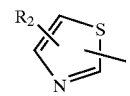

in which $R_2$ is a saturated or unsaturated 5- or 6-membered heterocycle containing from 1 to 3 hetero atoms chosen from nitrogen, oxygen and sulphur, optionally substituted with 1 or 2 substituents chosen from $C_1$–$C_3$ alkyl groups, hydroxyl groups, oxo (=O) groups, nitro groups, $C_1$–$C_3$ alkoxycarbonyl groups, aminocarbonyl groups, mono- or di- $C_1$–$C_3$ alkylaminocarbonyl groups and $C_1$–$C_3$ alkylcarbonyl groups; and pharmaceutically acceptable salts thereof.

The term "linear or branched $C_1$–$C_4$ alkyl groups" means a group chosen from methyl, ethyl, n-propyl, isopropyl, n-butyl, t-butyl, isobutyl and sec-butyl.

The term "saturated or unsaturated 5- or 6-membered heterocycle containing from 1 to 3 hetero atoms chosen from nitrogen, oxygen and sulphur" means heterocycles such as pyrrole, thiophene, furan, imidazole, pyrazole, thiazole, isothiazole, isoxazole, oxazole, pyridine, pyrazine, pyrimidine, pyridazine, triazole and thiadiazole, and partially or totally saturated forms thereof.

DETAILED DESCRIPTION OF THE INVENTION

Preferred compounds of formula (I) are compounds in which R and $R_1$ are the same or different hydrogen atom or methyl group.

Among this class, those compounds which are particularly preferred are compounds in which $R_2$ is a saturated or unsaturated 5- or 6-membered heterocycle containing from 1 to 3 hetero atoms chosen from nitrogen, oxygen and sulphur, optionally substituted with 1 or 2 substituents chosen from $C_1$–$C_3$ alkyl groups, hydroxyl groups, oxo (=O) groups, nitro groups and $C_1$–$C_3$ alkylcarbonyl groups.

Even more preferred compounds are those of formula (I) in which R and $R_1$ are the same or different hydrogen atom or methyl group and $R_2$ is a heterocycle chosen from thiazole, thiadiazole, thiophene, imidazole, isoxazole, triazole, pyrazole and oxazolidine, optionally substituted with a methyl group or with an =O group.

Among this class, those compounds which are particularly preferred are the compounds in which R and $R_1$ are hydrogen and the compounds in which R is methyl and $R_1$ is hydrogen.

Examples of pharmaceutically acceptable salts of the compounds (I) are salts with organic or inorganic acids such as hydrochloric acid, hydrobromic acid, hydriodic acid, nitric acid, sulphuric acid, phosphoric acid, acetic acid, tartaric acid, citric acid, benzoic acid, succinic acid and glutaric acid.

The preferred salt is the hydrochloride.

The compounds of formula (I) of the present invention can be prepared by various alternative synthetic methods similar to the method already described in patent application WO96/18633.

In particular, the compounds of formula (I) are synthesized by reacting an intermediate of formula

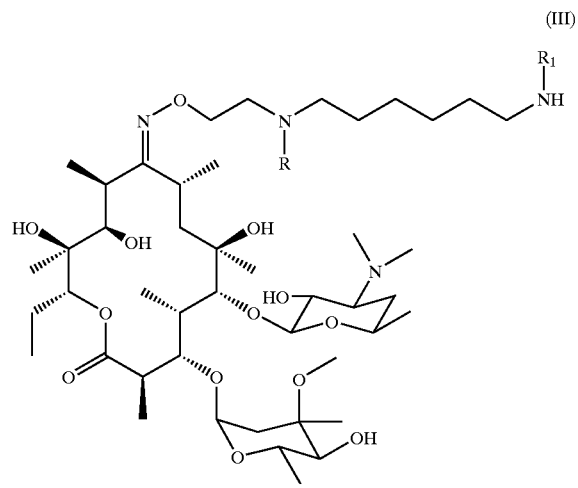

(III)

in which R and $R_1$ have the meanings given above; with an aldehyde of formula

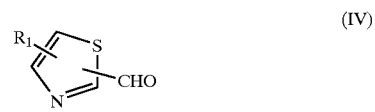

(IV)

in which $R_2$ has the meanings given above.

The intermediate of formula (III) can be prepared by alternative synthesis processes.

For example, a preferred process for preparing the intermediates of formula (III) in which R and $R_1$ are hydrogen atoms is given in the scheme below:

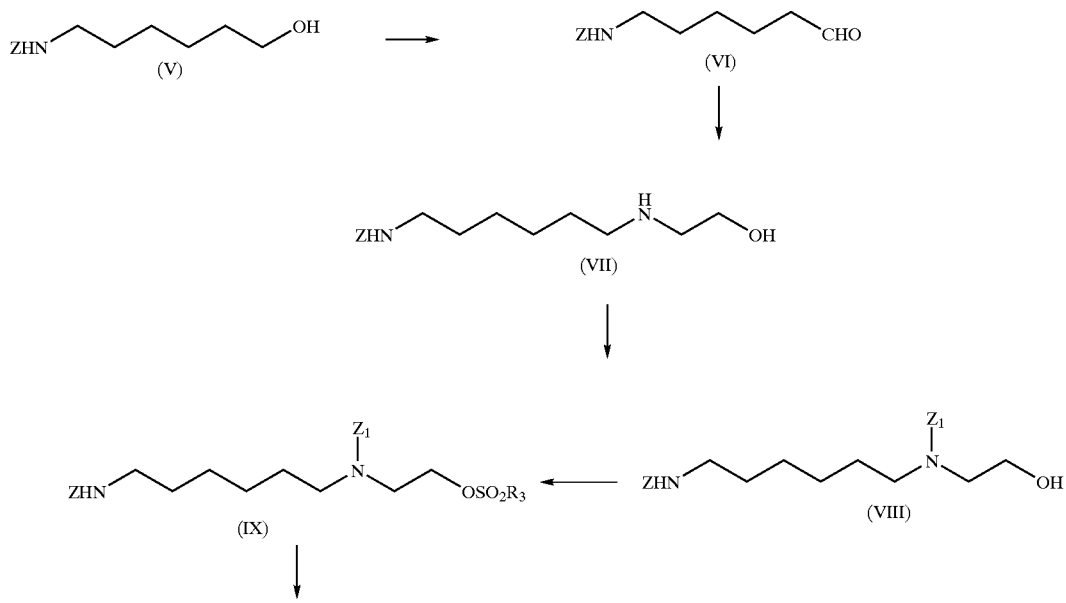

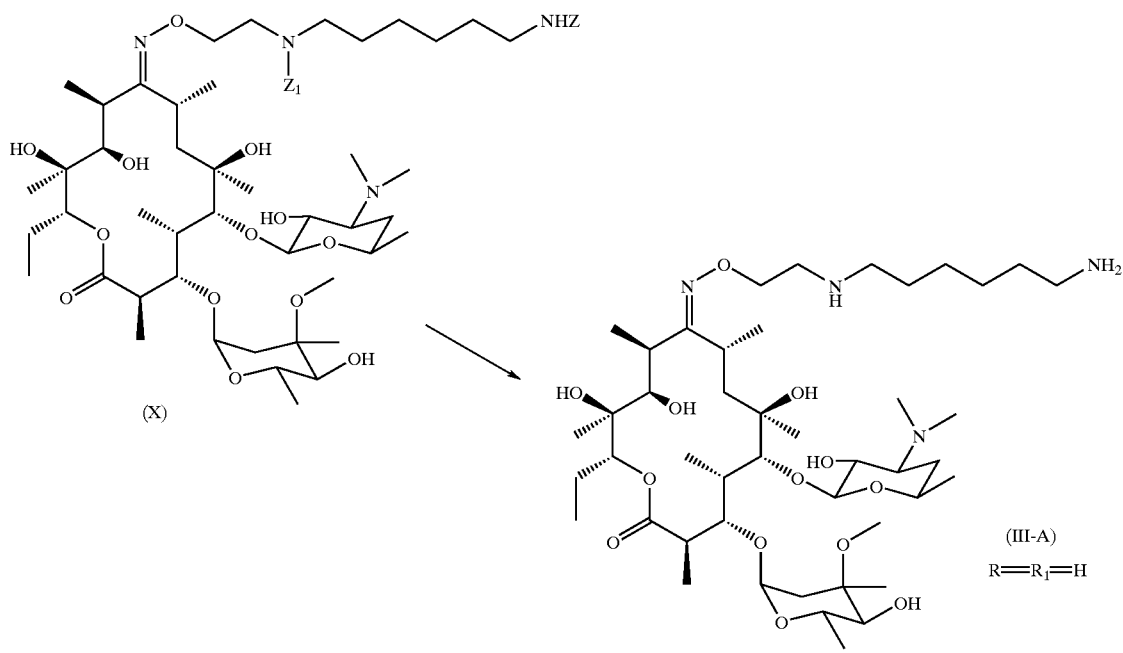

in which

Z and $Z_1$, the same or different, represent a protecting group;

$R_3$ represents a methyl or p-tolyl group.

The synthesis involves oxidation of the appropriately protected aminohexanol (V) into the corresponding aldehyde by treatment with an oxidizing agent, preferably sodium hypochlorite.

Condensation of the aldehyde (VI) with 2-aminoethanol followed by reduction of the intermediate imine, preferably with $NaBH_4$, gives compound (VII).

After also protecting the second amino group, compound (VIII) is treated with mesyl or tolyl chloride to activate the OH group and allow subsequent condensation of the activated compound (IX) with erythromycin A oxime. Removal of the protecting groups from compound (X) gives the intermediate (III-A).

Another preferred synthetic process for preparing the intermediates of formula (III) in which R is alkyl and $R_1$ is hydrogen is given in the scheme below:

Scheme 2

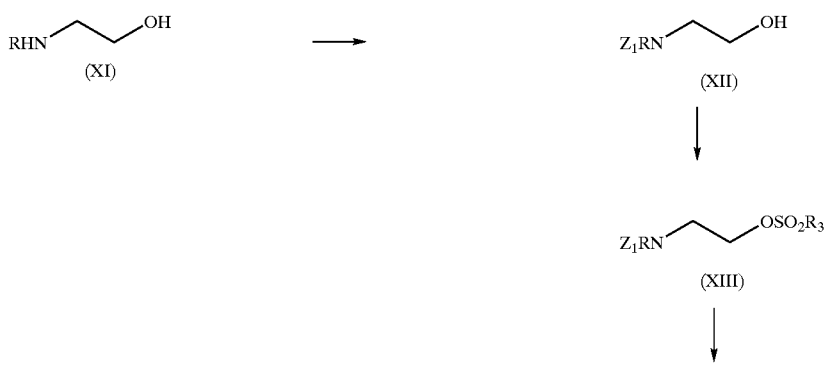

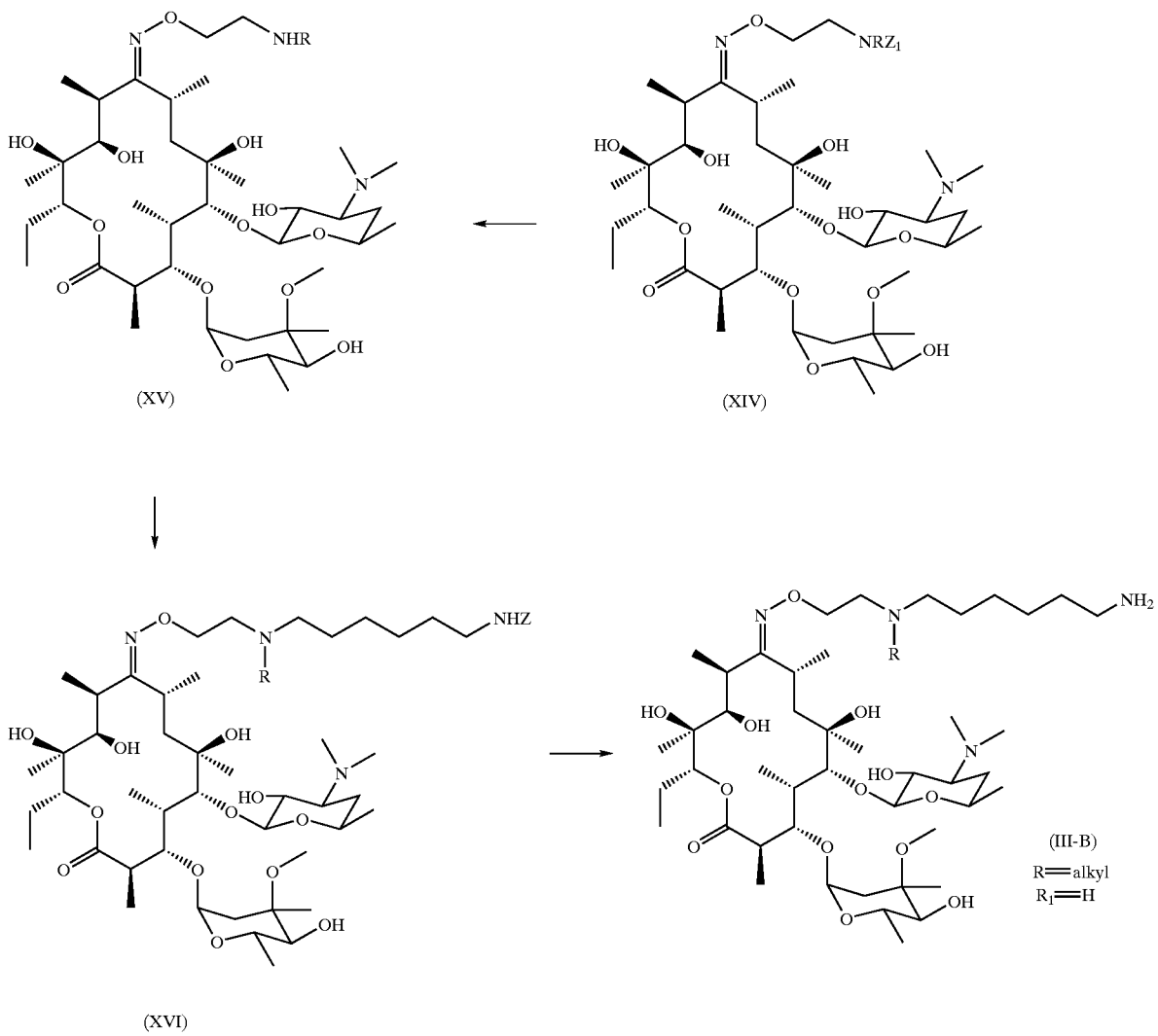

in which Z and $Z_1$ have the meanings given above and R is an alkyl group.

The synthesis involves firstly protecting the 2-amino ethanol (XI), and treatment of compound (XIII) with mesyl or tolyl chloride to activate the OH group and allow subsequent condensation of the activated compound (XIII) with erythromycin A oxime to give compound (XIV).

After deprotecting the amino group, compound (XV) is treated with compound (VI) and the intermediate (XVI) thus obtained is deprotected to give compound (III-B).

The compounds of formula (I) of the present invention have a broad spectrum of activity in vitro against Gram-positive and Gram-negative microorganisms.

This activity is greater than that of azithromycin on strains of Staphylococcus spp. and *Streptococcus pneumoniae* with inducible resistance to erythromycin (Example 21).

However, the aspect which mainly characterizes the compounds of the present invention is their appreciable duration of action in vivo. Specifically, as reported in Example 22, the therapeutic efficacy of the compounds of formula (I) was compared with that of clarithromycin.

It is clear from the comparison that the compounds of formula (I) have prolonged activity on the lungs, unlike clarithromycin.

The advantage of prolonged therapeutic efficacy is clear to those skilled in the art, since, from a practical viewpoint, it allows the dose of antibiotic to be reduced significantly and/or allows the interval between consecutive administrations to be increased, for example going from a prescription plan which involves two dosage intakes per day to a plan which involves only one dosage intake per day.

The compounds of formula (I) can be used in human and veterinary therapy.

For use in therapy, the compounds of formula (I) can be used in a pharmaceutical form which is suitable for oral or parenteral administration.

It is therefore a further object of the present invention to provide a pharmaceutical composition containing a therapeutically effective amount of a compound of formula (I) or of a salt thereof mixed with a pharmaceutically acceptable vehicle.

For the treatment of specific infections, the compounds of formula (I) may also be combined with a therapeutically effective amount of another active principle.

The following examples are now given for the purpose of illustrating the present invention more clearly.

In the examples, the abbreviation ERY is used to indicate the following erythromycin skeleton with the point of attachment at 9

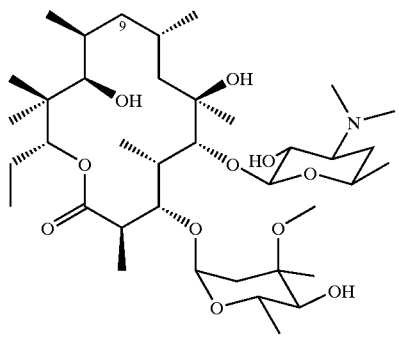

EXAMPLE 1

Preparation of benzyl [6-(2-hydroxyethylamino)hexyl]carbamate

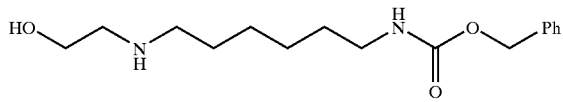

A solution of KBr (1.18 g; 9.94 mmol) in water (20 ml) and TEMPO (0.155 g; 0.994 mmol) were added to a solution of benzyl (6-hydroxyhexyl)carbamate (25 g; 99.47 mmol), prepared as described in patent application WO96/18633, in $CH_2Cl_2$ (350 ml), cooled with ice to about 10° C., followed by dropwise addition over about 15–20 minutes, while keeping the temperature at 10–12° C., of a solution prepared with $NaHCO_3$ (7.5 g; 89.28 mmol) and NaOCl (4.5% aqueous solution; 197 ml; 125 mmol).

15 minutes after the end of the dropwise addition, the phases were separated and the aqueous phase was extracted once with $CH_2Cl_2$ (100 ml). The combined organic extracts were washed twice with saline solution (20% NaCl) and dried over sodium sulphate.

3 Å molecular sieves (30 g) were added to the solution obtained (about 800 ml), followed by rapid dropwise addition, while cooling with water and ice, of a solution of 2-aminoethanol (35.9 ml; 0.597 mol) in ethanol (600 ml).

After completion of the dropwise addition, the mixture was stirred at room temperature for 2 hours and filtered.

$NaBH_4$ (4.54 g; 120 mmol) was added portionwise to the solution obtained, while stirring under a nitrogen atmosphere and cooling with water and ice.

At the end of the addition, the reaction mixture was stirred for 2 hours at room temperature and the solvent was then evaporated off.

The residue was taken up in water and ethyl acetate, the phases were separated and the aqueous phase was extracted twice more with ethyl acetate.

The combined organic extracts were washed with saline solution (20% NaCl), dried over sodium sulphate and concentrated to give an oily residue which solidified.

The residue was triturated from hexane, filtered off and washed with a mixture of hexane and ethyl ether to give the benzyl [6-(2-hydroxyethylamino)hexyl]carbamate (26.22 g; 89% yield) as a white solid.

$^1$H-NMR (CDCl$_3$) δ: 7.33–7.25 (m, 5H, Ar); 5.05 (s, 2H, COOCH$_2$); 4.96 (broad t, 1H, NH); 3.63–3.58 (m, 2H, *CH$_2$—OH); 3.19–3.09 (m, 2H, CH$_2$NCO); 2.72–2.67 (m, N—*CH$_2$—CH$_2$O); 2.59–2.52 (m, 4H, OH and CH$_3$); 1.53–1.23 (m, 8H, 4CH$_2$).

EXAMPLE 2

Preparation of benzyl 6-(benzyloxycarbonylaminohexyl)-(2-hydroxyethyl)carbamate

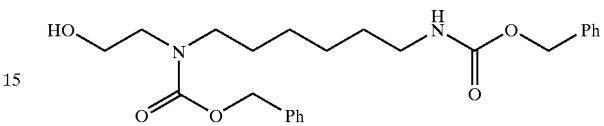

A solution of benzyl chloroformate (50% in toluene; 42.5 ml; 0.128 mol) in ethyl acetate (85.5 ml) and 1N NaOH (128 ml; 0.128 mol) were simultaneously added dropwise to a solution of the [6-(2-hydroxyethylamino)hexyl]carbamate ester (31.5 g; 0.107 mol) prepared as described in Example 1, in a mixture of water (87 ml), 1 N NaOH (17 ml) and ethyl acetate (180 ml), cooled to 0–5° C., while controlling the temperature and the pH (about 8).

After completion of the dropwise addition, the reaction mixture was stirred for 30 minutes at 0–5° C, the cooling was then removed and further 1N NaOH (15 ml) was added to bring the pH to 8, after which the mixture was left stirring overnight at room temperature.

The phases were separated and the aqueous phase was extracted once more with ethyl acetate. The combined organic extracts were washed with saline solution, dried over sodium sulphate and concentrated under vacuum to give an oily residue.

Chromatographic purification (eluent: from 60/40 to 70/30 ethyl acetate/petroleum ether) gave the benzyl 6-(benzyloxycarbonylaminohexyl)-(2-hydroxyethyl)carbamate as an oil (42.5 g; 92% yield).

$^1$H-NMR (CDCl$_3$) δ: 7.39–7.25 (m, 10H, Ar); 5.10 and 5.07 (2s, 4H, 2COOCH$_2$); 3.71 (broad signal, 2H, *CH$_2$—OH); 3.43–3.01 (m, 4H, 2CH$_2$NCO); 1.57–1.19 (m, 8H, 4CH$_2$).

EXAMPLE 3

Preparation of 2-[benzyloxycarbonyl(6-benzyloxycarbonylaminohexyl)amino]ethyl methanesulphonate

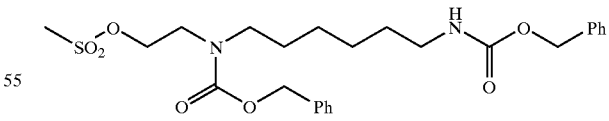

Triethylamine (8.95 ml; 64.31 mmol) was added to a solution of benzyl 6-(benzyloxycarbonylaminohexyl)-(2-hydroxyethyl)carbamate (13.78 g; 32.15 mmol) prepared as described in Example 2, in $CH_2Cl_2$ (140 ml). The mixture was cooled to 0–5° C. and a solution of methanesulphonyl chloride (3.36 ml; 43.41 mmol) in $CH_2Cl_2$ (20 ml) was then added dropwise.

After completion of the addition, the reaction mixture was stirred at room temperature for 60 minutes and then washed with 5% aqueous citric acid, with saline solution (20% NaCl), with 5% aqueous NaHCO₃ and finally again with saline solution. After drying over sodium sulphate and evaporation under vacuum, the 2-[benzyloxycarbonyl(6-benzyloxycarbonylaminohexyl)amino]ethyl methanesulphonate (16.37 g; 100% yield) was obtained as a brown oil.

$^1$H-NMR (CDCl₃) δ: 7.35–7.27 (m, 10H, Ar); 5.11 and 5.07 (2s, 4H, 2COOCH₂); 4.36–4.19 (m, 2H, CH₂OSO₂); 3.57–3.51 (m, 2H, SO—CH₂—*CH₂N); 3.32–3.07 (m, 4H, 2CH₂N); 2.91 and 2.85 (2s conformers, 3H, CH₃); 1.50–1.20 (m, 8H, 4CH₂).

EXAMPLE 4

Preparation of erythromycin A (E)-9-[O-[2[-benzyloxycarbonyl(6-benzyloxycarbonylaminohexyl)amino]ethyl]oxime

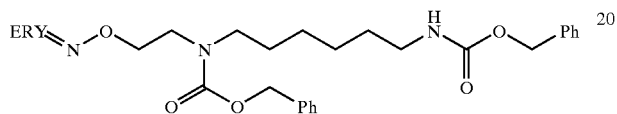

95% potassium tert-butoxide (4.178 g; 35.37 mmol) was added to anhydrous THF (165 ml) with stirring under a nitrogen atmosphere. After cooling with water and ice to about 10° C., erythromycin A oxime (24.08 g; 32.15 mmol) was added portionwise.

The reaction mixture was stirred for 30 minutes, 18-crown-6 ether (8.5 g; 32.15 mmol) was added, followed by addition of the 2-[benzyloxycarbonyl(6-benzyloxycarbonylaminohexyl)amino]ethyl methanesulphonate (16.37 g; 32.15 mmol), prepared as described in Example 3, in anhydrous THF (65 ml) and the mixture was left stirring at room temperature overnight.

After evaporation of the solvent, the residue was taken up in a mixture of ethyl acetate and saline solution (20% NaCl) and the phases were separated. The aqueous phase was extracted again with ethyl acetate. The combined organic extracts, washed twice with saline solution and dried, were concentrated under vacuum to give a foamy solid residue.

Chromatographic purification (eluent: 90/7/0.7 CH₂Cl₂/CH₃OH/NH₃) gave erythromycin A (E)-9-[O-[2-[benzyloxycarbonyl(6-benzyloxycarbonylaminohexyl) amino]ethyl]oxime] (27.1 g; 72% yield) as a foamy pale yellow solid.

$^1$H-NMR (CDCl₃) δ: 7.35–7.23 (m, 10H, Ar); 5.10 and 5.06 (2s, 4H, 2*COOCH₂); 3.29 (s, 3H, OMe); 2.26 (s, 6H, Me—N—Me).

EXAMPLE 5

Preparation of erythromycin A (E)-9-[O-[2-[(6-aminohexyl)amino]ethyl]oxime] (Intermediate A)

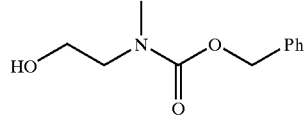

10% Pd/C (2.7 g) was added to a solution of erythromycin A (E)-9-[O-[2-[benzyloxycarbonyl(6-benzyloxycarbonylaminohexyl)amino]ethyl]oxime] (27.1 g; 23.37 mmol), prepared as described in Example 4, in ethanol (407 ml). The mixture was hydrogenated in a Parr hydrogenator. Once the consumption of H₂ was complete, the catalyst was filtered off and the solution was evaporated to give a foamy white solid residue.

Chromatographic purification (eluent: from 85/15/1.5 to 80/20/2 CH₂Cl₁/CH₃OH/NH₃) gave erythromycin A (E)-9-[O-[2-[(6-aminohexyl)amino]ethyl]oxime] (15.4 g; 74% yield) as a white solid.

$^1$H-NMR (CDCl₃) δ: 4.22–3.93 (m, 2H, NOCH₂); 3.28 (s, 3H, OMe); 2.25 (s, 6H, Me—N—Me).

EXAMPLE 6

Preparation of benzyl (2-hydroxyethyl) methylcarbamate

A solution of benzyl chloroformate (at 50% in toluene; 132.5 ml; 0.4 mol) in diethyl ether (267 ml) and 1N NaOH (400 ml; 0.4 mol) were simultaneously added dropwise to a two-phase solution of 2-methylamino-1-ethanol (25 g; 0.33 mol) in diethyl ether (390 ml) and water (312 ml), cooled to 0–5° C., while controlling the pH (about 8) and the temperature (not greater than 5° C.).

After completion of the addition, the reaction mixture was stirred for 30 minutes at 0° C. and then overnight at room temperature.

After separation of the phases, the aqueous phase was extracted once more with diethyl ether. The combined organic extracts were washed with saline solution (20% NaCl), dried over Na₂SO₄ and concentrated under vacuum to give an oily residue.

Chromatographic purification (eluent: from 1/1 to 70/30 ethyl acetate/petroleum ether) gave benzyl (2-hydroxyethyl) methylcarbamate (58 g; 84% yield) as an oil.

$^1$H-NMR (CDCl₃) δ: 7.37–2.27 (m, 5H, Ar); 5.11 (s, 2H, COOCH₂); 3.74 broad signal, 2H, CH₂O); 3.43 (t, 2H, CH₂N); 2.97 (s, 3H, Me); 2.44 (broad s, 1H, OH).

EXAMPLE 7

Preparation of 2-(benzyloxycarbonylmethylamino) ethyl methanesulphonate

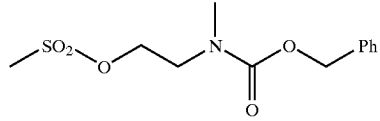

Triethylamine (4.32 ml; 31.06 mmol) was added to a solution of benzyl (2-hydroxyethyl)methylcarbamate (5 g; 23.89 mol), obtained as described in Example 6, in CH₂Cl₂ (50 ml). After cooling to 0–5° C., a solution of methanesulphonyl chloride (2.4 ml; 31.06 mmol) in CH₂Cl₂ (10 ml) was added dropwise over about 15 minutes and the reaction mixture was then stirred at room temperature.

After 3 hours, the solution was washed once with a mixture of saline solution (20% NaCl) and 10% HCl and then with saline solution to neutral pH.

After drying over Na₂SO₄ and concentrating under vacuum, 2-(benzyloxycarbonylmethylamino)ethyl methanesulphonate (7.08 g; quantitative yield) was obtained as an oil.

$^1$H-NMR (CDCl$_3$) δ: 7.37–7.29 (m, 5H, Ar); 5.12 (s, 2H, COOCH$_2$); 4.38–4.24 (m, 2H, N—CH$_2$—*CH$_2$); 3.60 (t, 2H, N—CH$_2$); 3.00 (s, 3H, SMe); 2.94 and 2.88 (2s conformers, 3H, NMe).

EXAMPLE 8

Preparation of erythromycin A (E)-9-[O-[2-[benzyloxycarbonylmethylamino]ethyl]oxime]

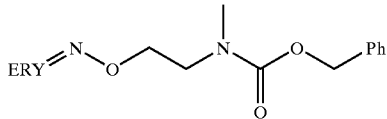

95% potassium tert-butoxide (4.34 g; 36.75 mmol) was added to anhydrous THF (170 ml), with stirring under a nitrogen atmosphere. After cooling to 5° C., erythromycin A oxime (25 g; 33.4 mmol) was added portionwise.

The reaction mixture was stirred at room temperature for 30 minutes and 18-crown-6 ether (8.83 g; 33.41 mmol) was added, followed by dropwise addition of a solution of 2-(benzyloxycarbonylmethylamino)ethyl methanesulphonate (9.6 g; 33.41 mmol), prepared as described in Example 7, in anhydrous THF (40 ml), with stirring at room temperature overnight.

After evaporation of the solvent, the residue was taken up in a mixture of ethyl acetate and water and the phases were separated. The aqueous phase was extracted with ethyl acetate. The combined organic extracts, washed with saline solution (20% NaCl) and dried, were concentrated under vacuum. The residue was taken up in hexane, triturated and concentrated again under vacuum to give a crystalline residue.

Chromatographic purification (eluent: 90/7/0.7 CH$_2$Cl$_2$/CH$_3$OH/NH$_3$) gave erythromycin A (E)-9-[O-[2-[benzyloxycarbonylmethylamino]ethyl]oxime] (23.3 g; 74% yield).

$^1$H-NMR (CDCl$_3$) δ: 7.37–7.26 (m, 5H, Ar); 5.11 (s, 2H, COOCH$_2$); 3.29 (s, 2H, OMe); 2.94 (s, 3H, CONMe); 2.32 (s, 6H, Me—N—Me)

EXAMPLE 9

Preparation of erythromycin A (E)-9-[O-[2-(methylamino)ethyl]oxime]

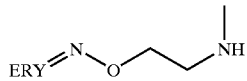

10% Pd/C (2.1 9) was added to a solution of erythromycin A (E)-9-[O-[2-[benzyloxycarbonylmethylamino]ethyl] oxime] (20.7 g; 22 mmol), prepared as described in Example 8, in ethanol (207 ml).

The mixture was hydrogenated in a Parr hydrogenator. Once the consumption of H$_2$ was complete, the catalyst was filtered off and the solution was evaporated to give a residue, which was taken up in and recrystallized from diethyl ether (125 ml) to give erythromycin A (E)-9-[O-[2-(methylamino) ethyl]oxime] (15 g; 84% yield).

$^1$H-NMR (CDCl$_3$) δ: 3.29 (s, 3H, OMe); 4.26–3.98 (m, 2H, NOCH$_2$); 2.43 (s, 3H, CH$_2$—N—*Me); 2.26 (s, 6H, Me—N—Me).

EXAMPLE 10

Preparation of erythromycin A (E)-9-[O-[2-[(6-benzyloxycarbonylaminohexyl)methylamino]ethyl] oxime]

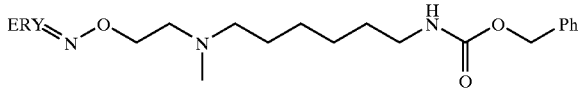

A solution of KBr (128 mg; 1.074 mmol) in water (2 ml) and TEMPO (17 mg; 0.107 mmol) was added to a solution of benzyl (6-hydroxyhexyl)carbamate (2.7 g; 10.74 mmol), prepared as described in patent application WO96/18633, in CH$_2$Cl$_2$ (38 ml), followed by dropwise addition, while keeping the temperature at about 15° C., of a solution prepared with NaHCO$_3$ (0.8 g; 9.56 mmol) and NaOCl (7.1% aqueous solution; 13.4 ml; 13.43 mmol).

15 minutes after the end of the dropwise addition, the phases were separated and the aqueous phase was extracted once with CH$_2$Cl$_2$. The combined organic extracts were washed with saline solution (20% NaCl) and dried over sodium sulphate.

The solution obtained from the above step (about 80 ml) was added dropwise to a solution of erythromycin A (E)-9-[O-[2-(methylamino)ethyl]oxime] (8.66 g; 10.74 mmol), prepared as described in Example 9, in CH$_2$Cl$_2$ (50 ml), stirred under a nitrogen atmosphere, followed by portionwise addition of 95% sodium triacetoxyborohydride (3.35 g; 15.04 mmol).

After completion of the addition, the mixture was stirred overnight at room temperature.

After addition of saline solution basified with K$_2$CO$_3$, the phases were separated and the aqueous phase was extracted with CH$_2$Cl$_2$. The combined organic extracts were washed twice with saline solution, dried over sodium sulphate and evaporated to dryness.

Chromatographic purification (eluent: 90/7/0.7 CH$_2$Cl$_2$/CH$_3$OH/NH$_3$) gave erythromycin A (E)-9-[O-[2-[(6-benzyloxycarbonylaminohexyl)methylamino]ethyl]oxime] (8.6 g; 77% yield).

$^1$H-NMR (CDCl$_3$) δ: 7.35–7.28 (m, 5H, Ar); 5.06 (s, 2H, COOCH$_2$); 3.29 (s, 3H, OMe); 2.31 (s, 6H, Me—N—Me); 2.18 (s, 3H, CH$_2$—N—Me).

EXAMPLE 11

Preparation of erythromycin A (E)-9-[O-[2-[(6-aminohexyl)methylamino]ethyl]oxime]
(Intermediate B)

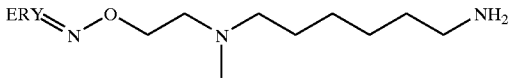

10% of Pd/C (0.55 g) was added to a solution of erythromycin A (E)-9-[O-[2-[(6-benzyloxycarbonylaminohexyl) methylamino]ethyl]oxime] (5.5 g; 5.29 mmol), prepared as described in Example 10, in ethanol (55 ml).

The mixture was hydrogenated in a Parr hydrogenator. Once the consumption of H$_2$ was complete, the catalyst was filtered off and the solution was evaporated to give a solid residue.

Chromatographic purification (eluent: 85/15/1.5 CH$_2$Cl$_1$/CH$_3$OH/NH$_3$) gave erythromycin A (E)-9-[O-[2-[(6- aminohexyl)methylamino]ethyl]oxime] (4.2 g; 87% yield) as a white solid.

$^1$H-NMR (CDCl$_3$) δ: 3.29 (s, 3H, OMe); 2.27 (s, 6H, Me—N—Me); 2.19 (s, 3H, CH—N—*Me).

EXAMPLE 12

Preparation of [2,4']bithiazolyl-2'-carbaldehyde (Intermediate C)

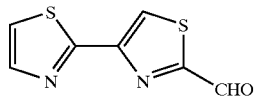

Step A

A solution of 1-thiazol-2-ylethanone (2.00 g; 15.7 mmol) in anhydrous THF (8 ml) was added to a solution of 97% phenyltrimethylammonium tribromide (6.08 g; 15.7 mmol) in anhydrous THF (32 ml).

The reaction mixture was heated at 35° C. for 3 hours and then left to stand overnight.

After filtering off the solid, the solution was concentrated under vacuum to give a residue which was dissolved in CH$_2$Cl$_2$ and purified by chromatography (eluent: 20/80 ethyl acetate/petroleum ether) to give 2-bromo-1-thiazol-2-ylethanone (2.85 g; 88% yield) as an oil which solidifies.

$^1$H-NMR (CDCl$_3$) δ: 8.03 (d, 1H, J$_{HH}$=2.8 Hz, —S—CH*=CH—N=); 7.75 (d, 1H, J$_{HH}$=2.8 Hz, —S—CH=CH*—N=); 4.70 (s, 2H, CH$_2$).

Step B

A mixture of 2-bromo-1-thiazol-2-ylethanone (2.85 g; 13.83 mmol) and 95% ethyl thiooxamate (1.94 g; 13.83 mmol) in ethanol (45 ml) was refluxed for 3 hours. After cooling and leaving to stand overnight, the precipitate was filtered off and washed with a small amount of ice-cold ethanol and with hexane to give ethyl [2,4']bithiazolyl-2'-carboxylate (2.33 g; 70% yield) as a solid (m.p. 143–145° C.).

$^1$H-NMR (CODC$_3$) δ: 8.20 (s, 1H, —CH*—S—C—COOC$_2$H$_5$); 7.86 (d, 1H, J$_{HH}$=2.8 Hz, —S—CH*=CH—N=); 7.41 (d, 1H, J$_{HH}$=2.8 Hz, —S—CH=CH*—N=); 4.50 (q, 2H, J$_{HH}$=7 Hz, CH$_2$); 1.45 (t, 3H, J$_{HH}$=7 Hz, CH$_3$).

Step C

NaBH$_4$ (0.66 g; 17.51 mmol) was added portionwise to a solution of ethyl [2,4']bithiazolyl-2'-carboxylate (2.2 g; 9.15 mmol), prepared as described in the above step, in anhydrous ethanol (440 ml), with stirring under a nitrogen atmosphere.

After 24 hours, the solvent was evaporated off under vacuum at about 30° C. to give a residue which was taken up in ethyl ether and saline solution (20% NaCl). The organic phase was separated out and washed once with saline solution. The combined aqueous phases were extracted again with ethyl ether.

The combined organic phases were dried and concentrated under vacuum. The residue was purified by chromatography (eluent: 1/1 ethyl acetate/petroleum ether) to give [2,4']bithiazol-2'-ylmethanol (1.53 g; 84% yield) as a white crystalline solid.

$^1$H-NMR (CDCl$_3$) δ: 7.92 (s, 1H, —CH*—S—C—CH$_2$OH); 7.81 (d, 1H, J$_{HH}$=3.2 Hz, —S—CH*=CH—N=); 7.33 (d, 1H, J$_{HH}$=3.2 Hz, —S—CH=CH*—N=); 4.99 (d, 2H, J$_{HH}$=6.2 Hz, CH$_2$); 3.24 (t, 1H, J$_{HH}$=6.2 Hz, OH).

Step D

A mixture of [2,4']bithiazol-2'-ylmethanol (1.53 g; 7.72 mmol), obtained as described in the above step, and MnO$_2$ (13.93 g; 160.2 mmol) in CH$_2$Cl$_2$ (76.5 ml) and methanol (7.65 ml) was stirred at room temperature for about 23 hours.

After filtration through Celite and evaporation of the solvent under vacuum, the semi-oily residue was dissolved in a mixture of CH$_2$Cl$_2$ and methanol, and purified by chromatography (eluent: 30/70 ethyl acetate/hexane).

The residue was triturated from hexane to give the intermediate C (0.9 g; 59.2% yield) as a crystalline solid (m.p. 106–108° C.).

$^1$H-NMR (CDCl$_3$) δ: 10.02 (d, 1H, J$_{HH}$=1.2 Hz, CHO); 8.31 (d, 1H, J$_{HH}$=1.2 Hz, —CH*—S—C—CHO); 7.87 (d, 1H, J$_{HH}$=4 Hz, —S—CH*=CH—N=); 7.42 (d, 1H, J$_{HH}$=4 Hz, —S—CH=CH*—N=).

EXAMPLE 13

Preparation of 2-(4-methyl[1,2,3]thiadiazol-5-yl) thiazole-4-carbaldehyde (Intermediate D)

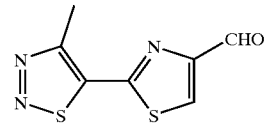

Step A

Ethyl 4-methyl[1,2,3]thiadiazole-5-carboxylate (4 g; 23.22 mmol) was added to a solution of NaOH (0.93 g; 23.22 mmol) in ethanol (50 ml) and water (4 ml).

The reaction mixture was stirred for about 1 hour.

After evaporation of the solvent and acidification, precipitation of the 4-methyl[1,2,3]thiadiazole-5-carboxylic acid as a white solid was observed, and this product (2.5 g) was filtered off.

The mother liquors were extracted with ethyl acetate and the combined organic extracts were dried and evaporated to dryness to give additional product (0.18 g). (Total, 2.68 g; 81% yield).

$^1$H-NMR (DMSO) δ: 2.84 (s, 3H, CH$_3$).

Step B

A suspension of 4-methyl[1,2,3]thiadiazole-5-carboxylic acid (1.65 g; 11.44 mmol), obtained as described in the above step, in SOCl$_2$ (10 ml) was refluxed for 2.5 hours.

After concentration of the solution under vacuum, the residue was taken up a few times in CH$_2$Cl$_2$, evaporating each time.

The oily residue obtained (1.9 g; 11.44 mmol) was dissolved in anhydrous THF (30 ml) and the solution was added dropwise and cautiously to a mixture of NH$_3$ gas in THF (150 ml), cooled to 0° C.

After the dropwise addition, the reaction mixture was stirred for 30 minutes at room temperature.

The solvent was evaporated off and the residue was taken up in a mixture of ethyl acetate and saline solution. The phases were separated and the aqueous phase was extracted twice more with ethyl acetate. The combined organic extracts, washed once with saline solution, were dried and concentrated under vacuum.

The solid residue obtained was triturated from a 20/80 ethyl ether/hexane mixture to give 4-methyl[1,2,3] thiadiazole-5-carboxamide (1.4 g; 85% yield) as a pale yellow solid.

$^1$H-NMR (DMSO) δ: 8.21–8.03 (2 broad signals, 2H, NH$_2$); 2.78 (s, 3H, CH$_3$).

Step C

A suspension of 4-methyl[1,2,3]thiadiazole-5-carboxamide (2.13 g; 14.87 mmol), prepared as described in the above step, and Lawesson's reagent (3.566 g; 8.81 mmol) in toluene (75 ml) was refluxed under a nitrogen atmosphere for 2 hours.

After cooling to room temperature and evaporation of the solvent, the orange-coloured semi-solid residue was purified by chromatography (eluent: 40/60 ethyl acetate/petroleum ether) to give 4-methyl[1,2,3]thiadiazole-5-carbothioic acid amide (2.14 g; 90% yield) as a yellow crystalline solid.

$^1$H-NMR (DMSO) δ: 10.52 and 9.79 (2 broad signals, 2H, NH$_2$); 2.72 (s, 3H, CH$_3$).

Step D

A mixture of 4-methyl[1,2,3]thiadiazole-5-carbothioic acid amide (2.1 g; 13.18 mmol), prepared as described in the above step, and ethyl bromopyruvate (1.98 ml; 15.82 mmol) in ethanol (250 ml) was refluxed for 4 hours and then stirred overnight at room temperature.

Filtration of the precipitated solid, washing with petroleum ether, gave ethyl 2-(4-methyl[1,2,3]thiadiazol-5-yl) thiazole-4-carboxylate (2.61 g; 77% yield).

$^1$H-NMR (CDCl$_3$) δ: 8.34 (s, 1H, CH thiazole); 4.44 (q, 2H, J$_{HH}$=7.2 Hz, CH$_2$); 3.00 (s, 3H, CH$_3$*); 1.42 (t, 3H, J$_{HH}$=7.2 Hz, —CH$_2$–CH$_3$*).

Step E

LiBH$_4$ (1.42 g; 65.25 mmol) was added, under nitrogen, to a solution of ethyl 2-(4-methyl[1,2,3]thiadiazol-5-yl) thiazole-4-carboxylate (2.38 g; 9.32 mmol), prepared as described in the above step, in anhydrous THF.

The reaction mixture was kept at room temperature for 3 hours and then poured cautiously into brine.

After stirring for 30 minutes, the phases were separated and the aqueous phase was extracted twice more. The residue obtained was purified by chromatography (eluent: 6/4 ethyl acetate/petroleum ether) to give a solid (1.56 g), which was triturated from ethyl ether to give [2-(4-methyl [1,2,3]thiadiazol-5-yl)thiazol-4-yl]methanol (1.26 g; 50% yield).

$^1$H-NMR (CDCl$_3$) δ: 7.44 (s, 1H, CH thiazole); 4.84 (s, 2H, CH$_2$); 2.95 (s, 3H, CH$_3$).

Step F

A mixture of [2-(4-methyl[1,2,3]thiadiazol-5-yl)thiazol-4-yl]methanol (1.06 g; 4.97 mmol) and MnO$_2$ (8.64 g; 99.39 mmol) in CH$_2$Cl$_2$ (100 ml) and methanol (10 ml) was refluxed for 6 hours.

After filtration through Celite and evaporation of the solvent, the residue was purified by chromatography (eluent: 40/60 ethyl acetate/petroleum ether) to give the intermediate D (0.88 g; 84% yield) as a white solid.

$^1$H-NMR (CDCl$_3$) δ: 10.11 (s, 1H, CHO); 8.35 (s, 1H, CH thiazole); 3.02 (s, 3H, CH$_3$).

EXAMPLE 14

Preparation of 2-thiophen-2-ylthiazole-4-carbaldehyde (Intermediate E)

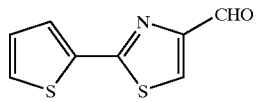

Step A

A solution of ethyl 2-thiophen-2-ylthiazole-4-carboxylate (0.883 g; 3.69 mmol) in anhydrous THF (10 ml) was added dropwise to a suspension of LiAlH$_4$(0.182 g; 4.8 mmol) in anhydrous THF (10 ml), at 0–5° C. under nitrogen.

After completion of the addition, the reaction mixture was stirred at room temperature for 90 minutes and then cooled to 0–5° C. and a 1/1 water/THF mixture (10 ml) was added cautiously. After dropwise addition of 20% NaOH (5 ml) and addition of water (15 ml), the mixture was stirred for 10 minutes and was then filtered through Celite, washing with ethyl ether.

The organic solution was washed with saline solution to neutral pH, dried and concentrated under vacuum to give (2-thiophen-2-ylthiazole-4-yl)methanol (0.65 g; 89% yield) as a pale yellow solid.

$^1$H=NMR (CDCl$_3$) δ: 7.51–7.47 (m, 1H, S—CH*=CH—CH=); 7.39–7.35 (m, 1H, S—CH=CH—CH*=); 7.09 (s, 1H, CH thiazole); 7.08–7.03 (m, 1H, S—CH=CH*—CH=); 4.77 (d, 2H, J$_{HH}$=6.4 Hz, CH$_2$); 2.4 (t, 1H, J$_{HH}$=6.4 Hz, OH).

Step B

TEMPO (5.1 mg; 0.0329 mmol) and a solution of KBr (39.2 mg; 0.329 mmol) in water (0.5 ml) were added to a solution of (2-thiophen-2-ylthiazole-4-yl)methanol (0.65 g; 3.29 mmol) in CH$_2$Cl$_2$ (12 ml), followed, after cooling to 0–5° C., by dropwise addition of a solution of 7.1% sodium hypochlorite (4.1 ml; 4.1 mmol) and NaHCO$_3$ (245 mg).

After stirring for about 1 hour under cold conditions, the phases were separated and the aqueous phase was extracted with CH$_2$Cl$_2$. The combined organic extracts were washed with saline solution (20% NaCl), dried and concentrated under vacuum to give an oily residue.

Chromatographic purification (20/80 ethyl acetate/ petroleum ether) gave the intermediate E (115 mg; 18% yield) as a solid.

$^1$H-NMR (CDCl$_3$) δ: 10.04 (s, 1H, CHO); 8.07 (s, 1H, CH thiazole); 7.60–7.55 (m, 1H, S—CH*=CH—CH=); 7.48–7.44 (m, 1H, S—CH=CH—CH*=); 7.13–7.07 (m, 1H, S—CH=CH*—CH=).

EXAMPLE 15

Preparation of 2-imidazol-1-ylthiazole-4-carbaldehyde (Intermediate F)

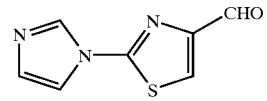

Step A

A mixture of ethyl 2-aminothiazole-4-carboxylate (13.30 g; 0.0772 mol) and 85% phosphoric acid (56.90 ml; 0.83 mol) was placed under mechanical stirring. After 15–20 minutes, the thick solution obtained was cooled to 5° C. and 65% HNO$_3$ (27.97 ml; 0.404 mol) was added dropwise.

At the end of the addition, the solution was cooled to −10° C. and a solution of sodium nitrite (8.82 g; 0.1278 mol) in water (15 ml) was added dropwise, while keeping the temperature below −5° C.

After stirring for about 1 hour at −10° C., a suspension of CuSO$_4$ (12.90 g; 0.0806 mol) and NaBr (22.65 g; 0.22 mol) in water (53 ml) was added portionwise with vigorous stirring.

At the end of the addition, vigorous stirring of the reaction mixture was maintained for 1 hour, allowing the temperature to rise to 10° C. At this point, NaHCO$_3$ (105.00 g; 1.25 mol) was added cautiously and portionwise, care being taken to limit the formation of foam by addition of ethyl acetate and water.

At the end of the addition, the mixture was stirred for 45 minutes and then diluted with ethyl acetate. The organic phase was separated out and the aqueous phase was extracted again with ethyl acetate. The combined organic extracts were washed with saline solution (20% NaCl).

After drying and evaporation to a residue under vacuum, the oily red-brown residue was purified by chromatography (20/80 ethyl acetate/petroleum ether) to give ethyl 2-bromothiazole-4-carboxylate (13.75 g; 75.4% yield)—m.p. 66–68° C.

$^1$H-NMR (CDCl$_3$) δ: 8.10 (s, 1H, CH thiazole); 4.40 (q, 2H, J$_{HH}$=7 Hz, CH$_2$); 1.38 (t, 3H, J$_{HH}$=7 Hz, CH$_3$).

Step B

Imidazole (0.95 g; 13.98 mmol) was added to a solution of 60% NaH (0.584 g; 14.61 mmol) in anhydrous DMF (10 ml), cooled to 15° C. under nitrogen. After heating at 60° C. for 5 minutes, the mixture was cooled to room temperature and a solution of ethyl 2-bromothiazole-4-carboxylate (3.00 g; 12.70 mmol) prepared as described in the above step, in anhydrous DMF (5 ml) was added dropwise and the solution was heated to 80° C.

After 3 hours at this temperature, the dark brown solution obtained was poured into water (700 ml) and extracted with ethyl acetate. The combined organic extracts were washed with saline solution (20% NaCl), dried and concentrated under vacuum.

The yellow crystalline residue was purified by chromatography (eluent: 95/5 CH$_2$Cl$_2$/CH$_3$OH) to give ethyl 2-imidazol-1-ylthiazole-4-carboxylate (1.8 g; 63.5% yield)—m.p. 107–109° C.

$^1$H-NMR (CDCl$_3$) δ: 8.22 (s, 1H, =N—CH*—N—); 7.96 (s, 1H, CH thiazole);thiazole); 7.54 (s, 1H, —N—CH*=CH—N-thiazole); 7.18 (s, 1H, —N—CH=CH*—N- 4.41 (q, 2H, J$_{HH}$=7 Hz, CH$_2$); 1.40 (t, 3H, J$_{HH}$=7 Hz, CH$_3$).

Step C

LiAlH$_4$ (0.102 g; 2.68 mmol) was added portionwise over about 60 minutes to a solution of ethyl 2-imidazol-1-ylthiazole-4-carboxylate (0.6 g; 2.68 mmol), prepared as described in the above step, in anhydrous THF (50 ml), cooled to 0° C.

After completion of the addition, the reaction mixture was kept for 1 hour at 0° C., after which water (5 ml) and THF (5 ml) were added. After basifying with 10% NaOH, and extraction with THF, the mixture was dried and evaporated under vacuum to give an oily residue which, after dissolving in CH$_2$Cl$_2$/CH$_3$OH and purification by chromatography (eluent: 95/5 CH$_2$Cl$_2$/CH$_3$OH), gave (2-imidazol-1-ylthiazol-4-yl)methanol (0.33 g; 68% yield) as a crystalline solid.

$^1$H-NMR (CDCl$_3$) δ: 8.30 (s, 1H, =N—CH*—N—); 7.47 (s, 1H, —N—CH*=CH—N-thiazole); 7.17 (s, 1H, N—CH=CH*—N-thiazole); 7.02 (s, 1H, CH thiazole); 4.72 (s, 2H, CH$_2$); 3.02 (broad signal, 1H, OH).

Step D

MnO$_2$ (3.28 g; 37.75 mmol) was added to a solution of (2-imidazol-1-ylthiazol-4-yl)methanol (0.33 g; 1.82 mmol), prepared as described in the above step, in CH$_2$Cl$_2$ (30 ml).

After stirring at room temperature for 24 hours, the mixture was filtered through Celite and evaporated under vacuum.

The residue was triturated from petroleum ether, filtered, washed and dried under vacuum at room temperature to give the intermediate F (0.268 g; 82% yield)—m.p. 143–146° C.

$^1$H-NMR (CDCl$_3$) δ: 9.95 (s, 1H, CHO); 8.22 (s, 1H, =N—CH*—N—); 7.98 (s, 1H, CH thiazole); 7.54 (s, 1H, —N—CH*=CH—N-thiazole); 7.21 (s, 1H, —N—CH=CH*—N-thiazole).

EXAMPLE 16

Preparation of 4-(3-methylisoxazol-5-yl)thiazole-2-carbaldehyde (Intermediate G)

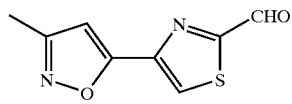

Step A

A first portion of phenyltrimethylammonium perbromide (14.466 g; 0.03836 mol) was added to a solution of 1-(3-methylisoxazol-5-yl)ethanone (48 g; 0.3836 mol) in CH$_2$Cl$_2$ (800 ml). The reaction was initiated with a few drops of HBr/CH$_3$COOH and addition of the phenyltrimethylammonium perbromide was completed (total 144.66 g; 0.3836 mol).

The reaction mixture was stirred at room temperature for 1 hour and then washed with water and dried.

Evaporation of the solvent gave a dark oil containing about 80% 2-bromo-1-(3-methylisoxazol-5-yl)ethanone which was used directly in the subsequent step.

$^1$H-NMR (CDCl$_3$) δ: 6.85 (s, 1H, CH isoxazole); 4.37 (s, 2H, CH$_2$); 2.35 (s, 3H, CH$_3$).

Step B

A solution of diethoxythioacetamide (6.65 g; 0.04077 mol) and 2-bromo-1-(3-methylisoxazol-5-yl)ethanone (10 g; 0.04077 mol), prepared as described in the above step, in absolute ethanol (31.3 ml) was kept overnight at room temperature and then refluxed for 30 minutes.

After evaporation of the solvent, the residue was taken up in acetone (235 ml) and 4N HCl (36 ml) and the solution was left to stand overnight.

After neutralization with NaHCO$_3$, filtration and evaporation, the residue was taken up in ethyl acetate and washed with water.

The orange-coloured solid residue obtained after drying, decolorization and evaporation was purified by chromatography (eluent: 9/1 hexane/ethyl acetate) to give the intermediate G (5 g; 63.1% yield) as a pale yellow solid—m.p. 116–117° C.

$^1$H-NMR (CDCl$_3$) δ: 10.03–10.00 (m, 1H, CHO); 8.14 (s, 1H, CH thiazole); 6.62 (s, 1H, CH thiazole); 2.37 (s, 3H, CH$_3$).

EXAMPLE 17

Preparation of 2-[1,2,4]triazol-1-ylthiazole-4-carbaldehyde (Intermediate H)

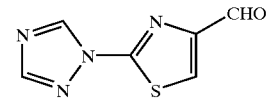

Step A 1,2,4-triazole (0.964 g; 13.97 mmol) was added to a suspension of 60% NaH (0.584 g; 14.61 mmol) in anhydrous DMF (10 ml), cooled with water and ice, and under nitrogen.

Once the effervescence had ended, a solution of ethyl 2-bromothiazole-4-carboxylate (3.00 g; 12.70 mmol), prepared as described in Example 15.A, in anhydrous DMF (5 ml) was added dropwise and the solution was heated to 80° C.

After 3 hours at this temperature, buffer at pH 7 (1 ml) was added and the solvent was evaporated off. The residue was taken up in brine and ethyl acetate and extracted three times. The combined organic extracts were dried and concentrated under vacuum to give ethyl 2-[1,2,4]triazol-1-ylthiazole-4-carboxylate (2.38 g; 83% yield) as a yellow solid.

$^1$H-NMR (CDCl$_3$) δ: 9.09 (s, 1H, N—CH*—N); 8.08 (s, 1H, N—CH*—N); 8.04 (s, 1H, CH thiazole); 4.42 (q, 2H, J$_{HH}$=7.2 Hz, CH$_2$); 1.40 (t, 3H, J$_{HH}$=7.2 Hz, CH$_3$).

Step B

Ethyl 2-[1,2,4]triazol-1-ylthiazole-4-carboxylate (1.0 g; 4.5 mmol) was added to a suspension of LiAlH$_4$ (170 mg; 4.5 mmol) in anhydrous THF (15 ml), cooled to 0° C.

After 45 minutes, a 1/1 water/THF mixture (6 ml) was added. After basifying with 20% NaOH (5 ml) and addition of water (50 ml), the mixture was stirred for 30 minutes, the solvent was evaporated off and the residue was taken up in saline solution and extracted with ethyl acetate. Drying and evaporation under vacuum gave a residue which, after chromatographic purification (eluent: 90/7 CH$_2$Cl$_2$/CH$_3$OH), gave (2-[1,2,4]triazol-1-ylthiazole-4-yl)methanol (0.36 g; 44% yield).

$^1$H-NMR (DMSO) δ: 9.33 (s, 1H, N—CH*—N); 8.33 (s, 1H, N—CH*—N); 7.41 (s, 1H, CH thiazole); 5.45 (t, 1H, J$_{HH}$=6.0 Hz, OH); 4.55 (d, 2H, J$_{HH}$=6.0 Hz, CH$_2$).

Step C

MnO$_2$ (5.3 g; 60.9 mmol) was added to a solution of (2-[1,2,4]triazol-1-ylthiazole-4-yl)methanol (0.32 g; 2.25 mmol), prepared as described in the above step, in chloroform (15 ml) and methanol (1.5 ml).

After stirring at room temperature for 24 hours, the mixture was filtered through Celite and evaporated under vacuum.

The beige-coloured residue was purified by chromatography (eluent: 50/50 ethyl acetate/petroleum ether) to give the intermediate H (0.310 g; 76% yield).

$^1$H-NMR (DMSO) δ: 9.87 (s, 1H, CHO); 9.47 (s, 1H, N—CH*—N); 8.70 (s, 1H, CH thiazole); 8.40 (s, 1H, N—CH*—N).

EXAMPLE 18

Preparation of 2-pyrazol-1-ylthiazole-4-carbaldehyde (Intermediate I)

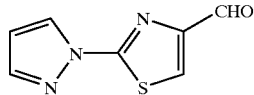

Step A

Pyrazole (0.95 g; 14 mmol) was added to a suspension of 60% NaH (0.58 g; 14.6 mmol) in anhydrous DMF (10 ml) cooled with water and ice, under nitrogen.

Once the effervescence had ended, a solution of ethyl 2-bromothiazole-4-carboxylate (2.945 g; 12.5 mmol), prepared as described in Example 15.A, in anhydrous DMF (5 ml) was added dropwise and the solution was heated to 80° C.

After 3 hours at this temperature, the solvent was evaporated off and the residue was taken up in brine and extracted with ethyl acetate. The combined organic extracts were dried and concentrated under vacuum to give a residue which, after chromatographic purification (eluent: 8/2 petroleum ether/ethyl acetate), gave ethyl 2-pyrazol-1-ylthiazole-4-carboxylate (1.45 g; 52% yield) as a white crystalline solid.

$^1$H-NMR (DMSO) δ: 8.56–8.53 (m, 1H, —N=CH*—CH=CH—N); 8.32 (s, 1H, CH thiazole); 7.91–7.89 (m, 1H, —N=CH—CH=CH*—N); 6.67–6.64 (m, 1H, —N=CH—CH*=CH—N); 4.31 (q, 2H, J$_{HH}$=7.0 Hz, CH$_2$); 1.30 (t, 3H, J$_{HH}$=7.0 Hz, CH$_3$).

Step B

LiAlH$_4$ (247 mg; 6.49 mmol) was added in 20 mg portions over 30 minutes to a solution of ethyl 2-pyrazol-1-ylthiazole-4-carboxylate (1.45 g; 6.49 mmol) in anhydrous THF (20 ml) cooled to 0° C. and under nitrogen. After 30 minutes, 10% NaOH (about 5 ml) and water (about 5 ml) were added to the reaction mixture. The mixture was stirred for 30–45 minutes, filtered through Celite and evaporated, and the residue was taken up in saline solution and ethyl acetate. Drying and evaporation under vacuum gave (2-pyrazol-1-ylthiazole-4-yl)methanol (1.13 g; 96% yield).

$^1$H-NMR (CDCl$_3$) δ: 8.31–8.27 (m, 1H, —N=CH*—CH=CH—N); 7.71–7.67 (m, 1H, —N=CH—CH=CH*—N); 6.94 (s, 1H, CH thiazole); 6.47–6.43 (m, 1H, —N=CH—CH*=CH—N); 4.70 (s, 2H, CH$_2$).

Step C

MnO$_2$ (10.8 g; 125 mmol) was added to a solution of (2-pyrazol-1-ylthiazole-4-yl)methanol (1.13 g; 6.24 mmol), prepared as described in the above step, in chloroform (100 ml).

After stirring at room temperature for 48 hours, the mixture was filtered through Celite and evaporated under vacuum.

The residue was triturated from petroleum ether to give the intermediate I (0.89 g; 80% yield).

$^1$H-NMR (CDCl$_3$) δ: 9.90 (s, 1H, CHO); 8.42–8.39 (m, 1H, —N=CH*—CH=CH—N); 7.94 (s, 1 H. CH thiazole); 7.74–7.72 (m, 1H, —N=CH—CH=CH*—N); 6.53–6.49 (m, 1H, —N=CH—CH*=CH—N).

EXAMPLE 19

Preparation of 2-(2-oxooxazolidin-3-yl)thiazole-4-carbaldehyde (Intermediate J)

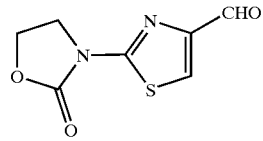

Step A

2-Oxazolidinone (1.97 g; 22.55 mmol) was added to a suspension of 60% NaH (0.943 g; 236 mmol) in anhydrous DMF (100 ml) at room temperature and under nitrogen.

Once the effervescence had ended, the solution was heated at 40° C. for 30 minutes and, while maintaining this temperature, a solution of ethyl 2-bromothiazole-4-carboxylate (4.84 g; 20.5 mmol), prepared as described in Example 15.A, in anhydrous DMF (10 ml) was added dropwise and the solution was heated to 60° C.

After 1 hour, buffer at pH 7 (10 ml) was added and the solvent was evaporated off. The residue was taken up in water and ethyl acetate, the organic phase was separated out and the aqueous phase was again extracted with ethyl acetate. The combined organic extracts were washed with saline solution, dried and concentrated under vacuum to give a residue which, after dissolving in a small amount of CH$_2$Cl$_2$ with a few drops of methanol, and on chromatographic purification (eluent: 7/3 petroleum ether/ethyl acetate), gave ethyl 2-(2-oxooxazolidin-3-yl)thiazole4-carboxylate (2.70 g; 54.3% yield) as a white crystalline solid of m.p. 157–159° C.

$^1$H-NMR (CDCl$_3$) δ: 7.84 (s, 1H, CH thiazole); 4.66–4.31 (m, 6H, 3CH$_2$); 1.37 (t, 3H, J$_{HH}$=7.1 Hz, CH$_3$).

Step B

BH$_3$.CH$_3$SCH$_3$ (1.4 ml; 14.56 mmol) was added dropwise to a suspension of ethyl 2-(2-oxooxazolidin-3-yl)thiazole-4-carboxylate (1.75 g; 7.22 mmol), prepared as described in the above step, in anhydrous THF (35 ml) at 50° C.

At the end of the addition, the reaction mixture was refluxed for 10 hours.

After cooling in water and ice to 0–5° C., methanol was added very cautiously.

The solution was concentrated under vacuum and the residue was purified by chromatography (eluent: 95/5 CH$_2$Cl$_2$/CH$_3$OH) to give 3-(4-hydroxymethylthiazole-2-yl) oxazolidin-2-one (0.56 g; 39% yield) as a white solid.

$^1$H-NMR (DMSO) δ: 7.01 (s, 1H, CH thiazole); 5.26 (t, 1H, OH); 4.58–4.11 (m, 6H, 3CH$_2$).

Step C

MnO$_2$ (7.2 g; 83.6 mmol) was added to a solution of 3-(4-hydroxymethylthiazole-2-yl)oxazolidin-2-one (0.56 g; 2.8 mmol), prepared as described in the above step, in chloroform (60 ml) and methanol (6 ml).

After stirring at room temperature for 24 hours, the mixture was filtered through Celite and evaporated under vacuum.

The residue was purified by chromatography (eluent: 80/20 ethyl acetate/petroleum ether) to give the intermediate J (0.53 g; 94% yield) as a white solid.

$^1$H-NMR (CDCl$_3$) δ: 9.84 (s, 1H, CHO); 7.89 (s, 1H, CH thiazole); 4.68–4.32 (m, 4H, 2CH$_2$).

EXAMPLE 20

Preparation of erythromycin A (E)-9-[O-[2-[6-[([2,4']bithiazole-2'-ylmethyl)amino]hexylamino]ethyl]oxime] (Compound 1)

R=R$_1$=H

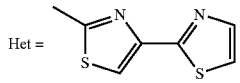

Intermediate C (0.196 g; 1 mmol) and 95% sodium cyanoborohydride (0.105 g; 1.6 mmol) were added, with stirring under a nitrogen atmosphere, to a solution of intermediate A (0.891 g; 1 mmol), prepared as described in Example 5, in CH$_2$Cl$_2$ (20 ml), followed by addition of a few drops of acetic acid to bring the pH to about 5.

The reaction mixture was stirred at room temperature for 5 hours under a nitrogen atmosphere.

After addition of water (50 ml) and acetic acid to bring the pH to about 4–5, the mixture was stirred for 30 minutes at room temperature. The acidic aqueous phase was separated out and basified cautiously with NaHCO$_3$ to a pH of about 8.

After extraction with CH$_2$Cl$_2$ and drying, the solvent was evaporated off to give a caramel-coloured residue which, on chromatographic purification (eluent: 90/10/1 CH$_2$Cl$_2$/CH$_3$OH/NH$_3$), gave compound 1 (0.38 g; 35.5% yield) as a caramel-coloured solid.

$^1$H-NMR (CDCl$_3$) δ: 7.84 (s, $_1$H, C—S—*CH=C); 7.78 (d, 1H, J$_{HH}$=3.6 Hz, N*CH=CH); 7.29 (d, 1H, N—CH=*CHS).

$^{13}$C-NMR (CDCl$_3$) δ: 173.87 (s), 163.03 (s), 149.22 (s), 143.59 (s, CHN); 119.29 (s, N—CH—*CHS); 115.85 (s, CH$_2$—C=S—*CH=C).

Working in a similar manner, the following compounds were prepared:

Erythromycin A (E)-9-[O-[2-[6-[([2,4']bithiazol-2'-ylmethyl)amino]hexyl]methylamino]ethyl]oxime] (Compound 2)

R=CH$_3$ R$_1$=H

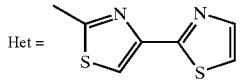

from intermediate B and intermediate C.

$^1$H-NMR (CDCl$_3$) δ: 7.85 (s, 1H, C—S*CH=C); 7.79 (d, 1H, J$_{HH}$=3.4 Hz, N*CH=CH); 7.30 (d, 1H, N—CH=*CHS); 2.17 (s, 3H, CH$_2$—N—*CH$_3$).

$^{13}$C-NMR (CDCl$_3$) δ: 173.89 (s), 163.05 (s), 149.24 (s), 143.61 (s, CHN); 119.29 (s, N—CH—*CHS); 115.85 (s, CH$_2$—C—S—*CH=C); 40.45 (s, CH$_2$—N—*CH$_3$).

Erythromycin A (E)-9-[O-[2-[6-[(2-[1,2,3] thiadiazol-5-ylthiazol-4-ylmethyl]amino] hexylamino]ethyl]oxime] (Compound 3).

R=R$_1$=H

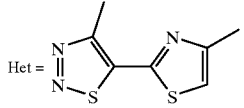

from intermediate A and intermediate D.

$^1$H-NMR (CDCl$_3$) δ: 7.34 (s, 1H, CHS); 2.93 (s, 3H, CH$_3$—C—N=N).

$^{13}$C-NMR (CDCl$_3$) δ: 158.21 (s); 155.22 (s); 154.59 (s); 144.27 (s); 117.31 (CHS); 14.41 (s, *CH$_3$—C—N=N).

Erythromycin A (E)-9-[O-[2-[6-[(2-thiophen-2-ylthiazol-4-ylmethyl)amino]hexylamino]ethyl] oxime] (Compound 4)

R=R$_1$=H

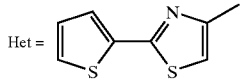

from intermediate A and intermediate E.

$^1$H-NMR (CDCl$_3$) δ: 7.46–7.00 (m, 3H, thiophene); 6.98 (s, 1H, CHS).

$^{13}$C-NMR (CDCl$_3$) δ: 161.76 (s, CN); 156.46 (s, S—C=N); 137.37 (s, CS); 127.82, 127.49 and 126.50 (3s, CH-thiophene); 113.71 (s, CHS-thiazole).

Erythromycin A (E)-9-[O-[2-[6-[(2-imidazol-1-ylthiazol-4-ylmethyl)amino]hexylamino]ethyl] oxime] (Compound 5).

R=R$_1$=H

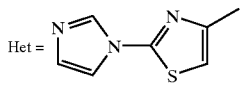

from intermediate A and intermediate F.

$^1$H-NMR (CDCl$_3$) δ: 8.12–7.11 (m, 3H, imidazole); 6.88 (s, 1H, CHS); 3.80 (s, 2H, *CH$_2$-thiazole).

$^{13}$C-NMR (CDCl$_3$) δ: 157.12 (s); 154.00 (s); 135.51 (s, N=CH—N); 130.78 (s, CH—N—CH=*CH); 117.66 (s, CH—N—*CH=CH); 110.71 (s, CHS).

Erythromycin A (E)-9-[O-[2-[6-[(2-imidazol-1-ylthiazol-4-ylmethyl)amino]hexyl]methylamino]ethyl]oxime] (Compound 6).

R=CH₃ R₁=H

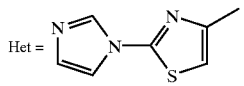

from intermediate B and intermediate F.
¹H-NMR (CDCl₃) δ: 8.12–7.11 (m, 3H, imidazole); 6.88 (s, 1H, CHS); 3.80 (s, 2H, *CH₂-thiazole); 2.15 (s, 3H, CH—N—*Me).
¹³C-NMR (CDCl₃) δ: 157.12 (s); 153.95 (s); 135.51 (s, N=CH—N); 130.78 (s, CH—N—CH=*CH); 117.66 (s, CH—N—*CH=CH); 110.72 (s, CHS); 49.66 (s, NMe).

Erythromycin A (E)-9-[O-[2-[6-[[2-(3-methylisoxazol-5-yl)thiazol-4-ylmethyl]amino]hexylamino]ethyl]oxime] (Compound 7)

R=R₁=H

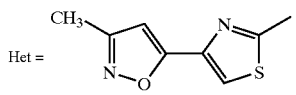

from intermediate A and intermediate G.
¹H-NMR (CDCl₃) δ: 7.67 (s, 1H, CHS); 6.44 (s, 1H, *CH=C—Me); 2.31 (s, 3H, *CH₃-isoxazole).
¹³C-NMR (CDCl₃) δ: 174.47 (s, CON); 165.02 (s); 160.33 (s); 143.62 (s); 117.85 (s, CHS); 101.51 (s, *CH=C—CH₃); 11.51 (s, CH₃).

Erythromycin A (E)-9-[O-[2-[6-[(2-[1,2,4]triazol-1-ylthiazol-4-ylmethyl)amino]hexylamino]ethyl]oxime] (Compound 8)

R=R₁=H

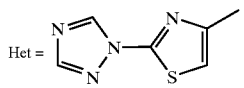

from intermediate A and intermediate H.
¹H-NMR (CDCl₃) δ: 8.92 (s, CHN); 8.04 (s, CHN); 7.03 (s, 1H, CHS); 3.84 (s, 2H, CH₂-thiazole).
¹³C-NMR (CDCl₃) δ: 153,71 (s); 152.88 (s); 141.14 (s); 113.04 (s, CHS).

Erythromycin A (E)-9-[O-[2-[methyl[6-[(2-[1,2,4]triazol-1-ylthiazol-4-ylmethyl)amino]hexylamino]ethyl]oxime] (Compound 9)

R=CH₃ R₁=H

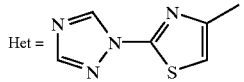

from intermediate B and intermediate H.
¹H-NMR (CDCl₃) δ: 8.92 (s, CHN); 8.04 (s, CHN); 6.98 (s, 1H, CHS); 3.80 (s, 2H, CH₂-thiazole); 2.15 (s, 3H, CH₂—N—*CH₃).

¹³C-NMR (CDCl₃) δ: 153.94 (s); 152.84 (s); 141.10 (s); 112.84 (s, CHS); 40.47 (s, NMe).

Erythromycin A (E)-9-[O-[2-[6-[(2-pyrazol-1-ylthiazol-4-ylmethyl)amino]hexylamino]ethyl]oxime] (Compound 10)

R=R₁=H

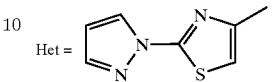

from intermediate A and intermediate I.
¹H-NMR (CDCl₃) δ: 8.30–6.41 (m, 3H, pyrazole); 6.82 (s, 1H, CHS); 3.79 (s, 2H, *CH₂-thiazole).
¹³C-NMR (CDCl₃) δ: 161.25 (s); 153.13 (s); 142.56 (s, thiazole-N—N—*CH); 127.40 (s, thiazole-N—*CH=CH—CH); 111.15 (s, CHS); 108.47 (s, N=CH—*CH=CH—N).

Erythromycin A (E)-9-[O-[2-[methyl[6-[(2-pyrazol-1-ylthiazol-4-ylmethyl]amino]hexyl]amino]ethyl]oxime] (Compound 11)

R=CH₃ R₁=H

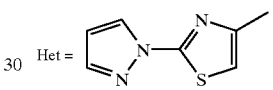

from intermediate B and intermediate I.
¹H-NMR (CDCl₃) δ: 8.30–6.40 (m, 3H, pyrazole); 6.82 (s, 1H, CHS); 3.79 (s, 2H, *CH₂-thiazole); 2.15 (s, 3H, CH—N*Me).
¹³C-NMR (CDCl₃) δ: 161.25 (s); 152.76 (s); 142.58 (s, thiazole-N—N—*CH); 127.41 (s, thiazole-N—*CH=CH—CH); 111.40 (s, CHS); 108.50 (s, N=CH—*CH=CH—N); 40.46 (s, NMe).

Erythromycin A (E)-9-[O-[2-[6-[[2-(2-oxooxazolidin-3-yl)thiazol-4-ylmethyl]amino]hexylamino]ethyl]oxime] (Compound 12)

R=R₁=H

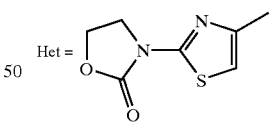

from intermediate A and intermediate J.
¹H-NMR (CDCl₃) δ: 6.72 (s, 1H, CHS); 4.58–4.22 (m, 4H, O—*CH—*CH₂—N); 3.71 (s, 2H, *CH₂-thiazole).
¹³C-NMR (CDCl₃) δ: 157.85 (s); 154.55 (s); 150.93 (s); 109.65 (s, CHS).

EXAMPLE 21

In vitro Antibacterial Activity

The minimum inhibitory concentrations (MIC), with respect to Gram-positive bacteria (erythromycin-sensitive and -resistant strains) and Gram-negative bacteria, were determined by means of the broth-scaler dilution micromethod in twin series [National Committee for Clinical Laboratory Standards, 1990; Methods for dilution antimicrobial susceptibility tests for bacteria that grow aerobically; Approved standards M7-A2-NCCLS, Villanova, Pa.], using Mueller Hinton Broth (MHB) as culture medium.

In the case of Streptococcus pneumoniae, the medium was supplemented with 5% horse serum.

Azithromycin [The Merck Index, XIIth Edition, No. 946) was used as reference macrolide.

The MIC values, expressed in µg/ml, were determined after incubating the microplates at 37° C. for 18 hours, by evaluating the lowest concentration of antibiotic capable of inhibiting bacterial growth.

Charles River albino mice (strain CD1) weighing 23–25 g were used, kept in groups of 6 to a cage and fed normally with a standard diet and water ad libitum.

A suspension of *Streptococcus pyogenes* C203 (equal to about $10^8$ CFU) in tryptone broth (0.05 ml) was administered intranasally to each mouse, anaesthetized with a mixture of ethyl ether and chloroform.

The compounds of formula I and the clarithromycin reference compounds were administered orally in a single dose, as a 0.5% suspension Methocel® 1 hour after the infection and 24 hours before the infection.

Observation of the death of the mice was continued for 7 days after the infection.

TABLE 1

In vitro antibacterial activity, expressed as MIC (µg/ml), of the compounds of formula (I) and of azithromycin, with respect to erythromycin-resistant strains of *Staphylococcus spp.*

| | MIC (µg/ml) | | | | | |
|---|---|---|---|---|---|---|
| Compound | S. aureus 929 | S. coag. Neg. 845 | S. epidermis 60* | S. specie 916* | S. aureus 77 | S. haemolyticus 161 |
| 1 | >64 | >64 | 2 | 2 | >64 | >64 |
| 2 | >64 | >64 | 2 | 4 | >64 | >64 |
| 3 | 64 | 64 | 1 | 0.5 | >64 | 64 |
| 4 | 16 | 16 | 0.5 | 8 | 64 | 16 |
| 5 | >64 | >64 | 1 | 4 | >64 | >64 |
| 6 | >64 | >64 | 2 | 4 | >64 | >64 |
| 8 | >64 | >64 | 2 | 8 | >64 | >64 |
| 10 | 32 | 32 | 1 | 4 | >64 | 64 |
| 11 | >64 | >64 | 2 | 8 | >64 | >64 |
| Azithromycin | >64 | >64 | >64 | >64 | >64 | >64 |

*Erythromycin-resistant (inducible) *Staphylococcus spp.*

TABLE 2

In vitro antibacterial activity, expressed as MIC (µg/ml) of the compounds of formula (I) and of azithromycin, with respect to erythromycin-resistant strains of *Streptococcus pneumoniae*.

| | MIC (µg/ml) | | |
|---|---|---|---|
| Compound | S. pneumoniae 1035 | S. pneumoniae 1047 | S. pneumoniae 1051 |
| 5 | 4 | 4 | 2 |
| 6 | 0.5 | 1 | 0.25 |
| 8 | 4 | 2 | 1 |
| 10 | 1 | 0.5 | 0.25 |
| 11 | 0.0625 | 0.5 | 0.125 |
| Azithromycin | 4 | 2 | 16 |

The data given in Tables 1 and 2 show that the spectrum of activity of the compounds of formula (I) of the present invention is particularly broad and also includes erythromycin-resistant microorganisms.

EXAMPLE 22

In vivo Antibacterial Activity

The therapeutic efficacy, expressed as the 50% protective dose ($PD_{50}$), of the compounds of formula (I) was evaluated in the experimental pulmonary infection induced in mice by *Streptococcus pyogenes* C203.

The $PD_{50}$, expressed as µmol/kg, was calculated by means of probit analysis.

TABLE 3

In vivo therapeutic efficacy of the compounds of formula (I) and of the clarithrmycin reference compound after oral administration.

| | $PD_{50}$ (µmol/kg) | |
|---|---|---|
| Compound | 1 hour after infection | 24 hours before infection |
| 1 | 22.9 | 15.5 |
| 3 | 4.5 | 25.4 |
| 4 | 11.4 | 14.3 |
| 6 | 10.1 | 16.0 |
| 11 | 11.2 | 25.4 |
| Clarithromycin | 7.38 | >85.6 |

It is seen from the data given in the table that the compounds of formula (I) have prolonged activity on the lungs, unlike clarithromycin.

What is claimed is:

1. A compound of formula:

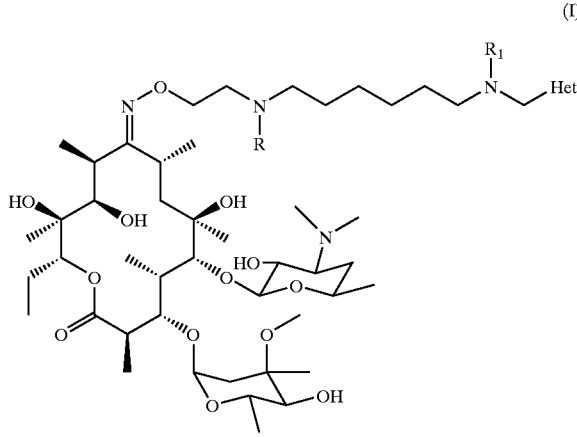

(I)

wherein
R is hydrogen or a linear or branched $C_1$–$C_4$ alkyl group;
$R_1$ is hydrogen or a linear or branched $C_1$–$C_4$ alkyl group;
Het is a biheterocyclic group of formula

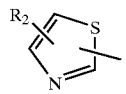

wherein
$R_2$ is a saturated or unsaturated 5- or 6-membered heterocycle containing from 1 to 3 heteroatom(s) selected from the group consisting of nitrogen, oxygen and sulphur, optionally substituted with 1 or 2 substituents selected from the group consisting Of $C_1$–$C_3$ alkyl, hydroxyl, oxo (=O), nitro, $C_1$–$C_3$ alkoxycarbonyl, aminocarbonyl, mono- or di-$C_1$–$C_3$ alkylaminocarbonyl and $C_1$–$C_3$ alkylcarbonyl; or a pharmaceutically acceptable salt thereof.

2. The compound according to claim 1, wherein R and $R_1$ are independently selected from the group consisting of hydrogen and methyl.

3. The compound according to claim 1, wherein $R_2$ is a saturated or unsaturated 5- or 6- membered heterocycle containing from 1 to 3 heteroatom(s) selected from the group consisting of nitrogen, oxygen and sulphur, optionally substituted with 1 or 2 substituents selected from the group consisting of $C_1$–$C_3$ alkyl, hydroxyl, oxo, nitro and $C_1$–$C_3$ alkylcarbonyl.

4. The compound according to claim 1, wherein R and $R_1$ are independently selected from the group consisting of hydrogen and methyl and $R_2$ is a heterocycle selected from the group consisting of thiazole, thiadiazole, thiophene, imidazole, isoxazole, triazole, pyrazole and oxazolidine, optionally substituted with methyl or with oxo.

5. The compound according to claim 1, wherein R and $R_1$ are hydrogen.

6. The compound according to claim 1, wherein R is methyl and $R_1$ is hydrogen.

7. A process for preparing the compound of claim 1, comprising:
reacting an intermediate of formula

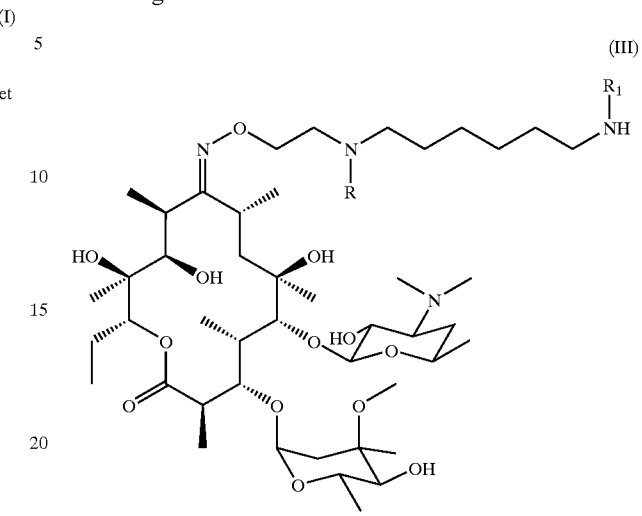

(III)

wherein R and $R_1$ are defined in claim 1;
with an aldehyde of formula

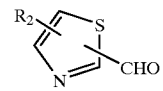

wherein $R_2$ is defined in claim 1.

8. A composition comprising the compound according to claim 1 and a pharmaceutically acceptable vehicle.

9. The composition of claim 8 in a form suitable for oral administration.

10. The composition of claim 8 in a form suitable for parenteral administration.

11. The composition of claim 8, further comprising one or more other active principle(s).

12. A method for inhibiting bacterial growth comprising contacting a bacterium with the compound of claim 1.

13. A method for treating a bacterial infection comprising administering to a subject in need thereof the compound of claim 1.

14. The method of claim 13 comprising administering said compound to a non-human animal.

15. The method of claim 13 comprising administering said compound to a human.

16. The method of claim 13 comprising treating a gram positive bacterial infection.

17. The method of claim 13 comprising treating a Staphylococcal infection.

18. The method of claim 13 comprising treating a Streptococcal infection.

19. The method of claim 13 comprising treating a gram negative bacterial infection.

20. The compound of claim 1 in the form of a hydrochloride.

* * * * *